United States Patent [19]

Aiba et al.

[11] Patent Number: 4,695,546
[45] Date of Patent: Sep. 22, 1987

[54] **TRANSFORMING *BACILLUS STEAROTHERMOPHILUS* WITH PLASMID VECTOR PTB 19**

[75] Inventors: Shuichi Aiba; Tadayuki Imanaka, both of Suita, Japan

[73] Assignee: Shionogi & Co., Ltd., Osaka, Japan

[21] Appl. No.: 356,150

[22] Filed: Mar. 8, 1982

[30] Foreign Application Priority Data

Mar. 6, 1981 [JP] Japan ................................. 56-32809
Mar. 6, 1981 [JP] Japan ................................. 56-32810

[51] Int. Cl.[4] ............................................ C12N 15/00
[52] U.S. Cl. ................................ 435/172.3; 435/317; 935/27; 935/56
[58] Field of Search .............. 435/68, 172, 317, 172.3, 435/317; 935/27

[56] References Cited

U.S. PATENT DOCUMENTS 4,237,224 12/1980 Cohen et al. ........................ 435/172

OTHER PUBLICATIONS

Bingham et al, Characterization of *Bacillus stearothermophilus* Plasmid pAB124 and Construction of Deletion Variants, *J. of General Microbiology* (1980), 119, 109-115, Dobritsa et al, [Chem. Abst. 89:87026x, 1978, p. 87027.

Primary Examiner—Sidney Marantz
Attorney, Agent, or Firm—Wenderoth, Lind & Ponack

[57] ABSTRACT

A process for transformation of a microorganism by introduction of a plasmid therein, the microorganism being thermophilic and gram-positive or gram-variable, and vector plasmids used therefor.

1 Claim, 2 Drawing Figures (A)

(B)

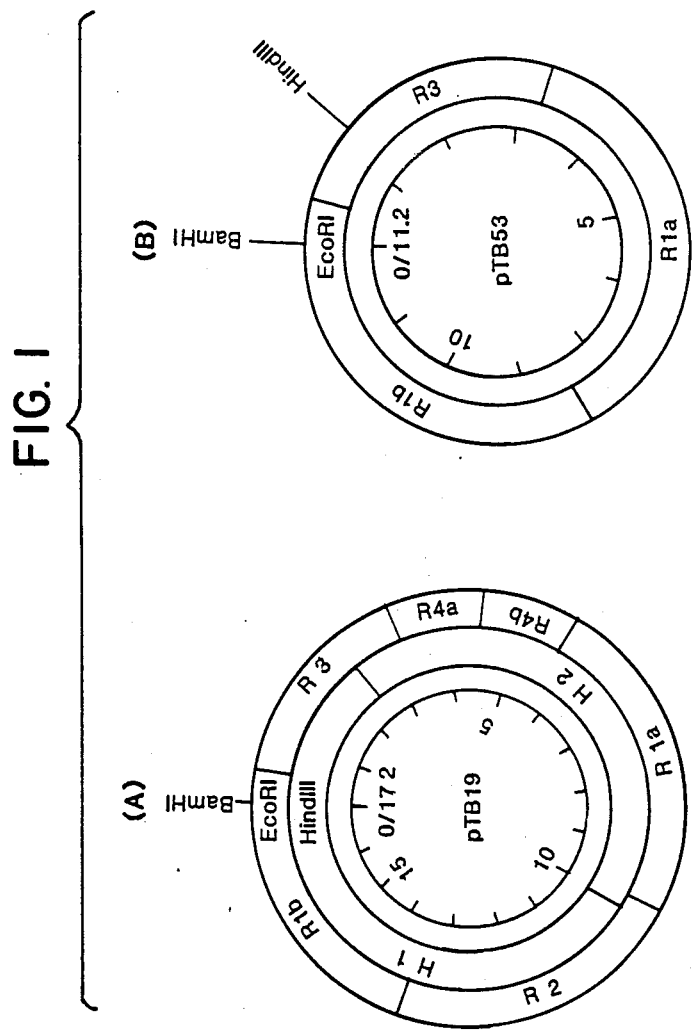

TRANSFORMING BACILLUS STEAROTHERMOPHILUS WITH PLASMID VECTOR PTB 19

The present invention relates to a process for transforming host microorganisms by means of plasmid introduction, and particularly to a process for transforming gram-positive or gram-variable thermophilic bacteria and vector plasmids used therefor.

Transformation of host microorganisms by means of plasmid introduction itself is generally known as a conventional method employed for endowing a given host microorganism with a new genetic character foreign (not inherent) to said host microorganism. However, it has not been reported that such a method can also be applicable to the transformation of the thermophilic bacteria.

If a desired genetic character, i.e. an ability for producing a useful substance, could be given to the thermophilic bacterial inherently having a high proliferating rate and an ability of producing heat-resistant enzymes, especially to those normally growing at 55° C. or above, a number of advantages could be brought about. One of the advantages is that such transformed bacteria can be cultivated at an elevated temperature and, therefore, can be protected from contamination hazards attributable to mesophilic bacteria and/or bacteriophage in their fermentation processes. Another advantage is that a great deal of reduction of energy can be achieved for cooling a fermentation tank. In addition, various processes for transforming bacteria, such as protoplastization of the host bacteria, introduction of a plasmid into the host cell and regeneration of the cell walls, could be performed at an elevated temperature which permits normal growth of the thermophilic bacteria. Therefore, contamination hazards during each of the processes could be reduced, and a pure transformed strain could be easily constructed.

Bingham A.H.A et al. found *Bacillus stearothermophilus* carrying a known plasmid pAB124 resistant to tetracycline (hereinafter referred to as "Tc$^r$") and used this plasmid pAB124 in an attempt to transform a thermophilic bacterium. However, no transformant could be obtained (J. Gen. Microbiol., 114, pp.401–408, 1979 and 119, pp. 109–115, 1980).

It has now been found that various thermophilic bacteria can be transformed by means of a variety of vector plasmids, any of such plasmids can be retained with sufficient stability in the host microorganism at an elevated temperature and genetic character carried by the plasmid can be successfully expressed in the host cell.

Accordingly, one of the objects of the present invention is to provide a novel method of transforming gram-positive or gram-variable thermophilic bacteria by means of plasmid introduction.

Another object of the invention is to provide a series of vector plasmids especially useful for this purpose.

The gram-positive or gram-variable thermophilic bacteria which can be used as the host microorganisms in the process of the present invention include those capable of growing and proliferating at a temperature above 40° C. Those belonging to genus Bacillus are particularly preferred for the purpose.

As well known in the art, there exist bacteria which belong to genus Bacillus whose gram-staining property is indefinite and vary with ambient conditions. Such bacteria are hereinafter referred to as "gram-variable" bacteria and included in the scope of the present invention. The structures of the surface layers of the cell of such bacteria are identical with those of normal gram-positive bacteria. Namely, the gram-variable bacteria have a cell wall (peptidoglycan zone) with an inside (cytoplasmic) membrane, but, lack an outer membrane.

Typical thermophilic bacteria are *Bacillus stearothermophilus* ATCC 12980 CU12 (temperature for growth: minimum, 30°–40° C.; maximum, 65°–75° C.), *Bacillus coagulans* (temperature for growth: minimum, 15°–25° C.; maximum, 65°–75° C.) and *Bacillus brevis* (temperature for growth: minimum, 10°–35° C.; maximum, 40°–60° C.). However, this exemplification should not be construed to limit the scope of the invention.

According to the present invention, transformation of host microorganisms is principally carried out at a temperature ranging from 40° to 70° C., and particularly, at about 48° C. By performing the transforming processes in this manner, it is possible to effectively avoid any contamination hazards attributable to other microorganisms which can not survive at such a high temperature.

Preferred vector plasmids for transforming thermophilic bacteria are a known plasmid pUB110 derived from *Staphylococcus aureus* (available from Bethesda Research Laboratoris Inc.), and our novel plasmids *pTB*19, pTB53 and pTT32.

A novel plasmid pTB19 has been obtained from a bacterium found in a high temperature environment. Although the bacterium has not been identified yet, it has been found that the plasmid pTB 19 is resistant to tetracycline and kanamycin (hereinafter referred to as "Tc$^r$" and "Km$^r$"). *Bacillus subtilis* strain 168 (trpC2) retaining the plasmid pTB19 was deposited with the Fermentation Research Institute in Japan and assigned FERM-P 5895.

A novel plasmid pTB53, which is smaller and more usable plasmid than pTB19, has been obtained by breakage and recombination of the latter.

pTTB32, which is also a novel plasmid constructed by us, has been obtained by combining pTB53 with a hybrid plasmid which has been constructed by combining a plasmid pMB9 derived from *Escherichia coli* with a DNA segment carrying a penicillinase producing gene extracted from *Bacillus licheniformis*.

Hereinafter, the present invention will be described in connection with preferred embodiments thereof. However, it is to be noted that the following description of the preferred embodiments of the present invention is only for the purpose of illustration and will, therefore, be made as utilizing known microorganisms and chemicals readily available from any one of authorized public depositories and any of commercial drug stores, respectively, and also known manipulating methods readily available from prior art publications. Accordingly, the preferred embodiments of the present invention herein disclosed should not be construed as set forth for the purpose of limiting the spirit and scope of the present invention.

In the preferred embodiment, *Bacillus stearothermophilus* ATCC 12980, which is a typical gram-positive thermophilic bacteria, has been selected as the host microorganisms (receptor bacteria). This microorganism can grow and proliferate at a temperature ranging from 40° to 70° C. and holds a cryptic plasmid pBS01 therein. One of their spontaneous mutant strains, CU11, has a chromosomal DNA carrying a gene resistant to streptmycin (hereinafter referred to as "Sm$^r$") and lack the cryptic plasmid pBS01.

On the other hand, the plasmid pUB110 (Km$^r$) is used as a donor plasmid, which is of *Staphylococcus aureus* origin and has been extracted from *Bacillus subtilis.*

This plasmid pUB110 (Km$^r$) is allowed to coexist with *Bacillus stearothermophilus* which had previously been protoplastized by means of lysozyme treatment. The mixture is allowed to coagulate in the presence of polyethylene glycol (hereinafter referred to as "PEG") in a hypertonic medium containing sucrose, and then allowed to regenerate cell walls in a hypertonic agar-containing medium. Introduction of the plasmid into the host cell is thus completed. By incorporation of kanamycin, for screening purpose, in the medium used in the regeneration step, a transformed strain (Km$^r$, Sm$^r$) of *Bacillus stearothermophilus* is obtained.

Since the processes of protoplastization, coagulation and cell wall regeneration, except for the separation steps interposed therebetween, are carried out at a temperature ranging from 40° to 70° C., the transformed strain can easily be obtained without contamination by other microorganisms.

In another preferred embodiment of the invention, the same host microorganisms as mentioned above and a plasmid described below are employed. Namely, a chromosomal DNA fragment including a gene of penicillinase producing activity and derived from *Bacillus licheniformis* ATCC 9945A FDO 120 is first cloned within cells of *Escherichia coli.* The cloned gene is inserted into a vector plasmid pTB53 and the resultant hybrid plasmid is introduced into *Bacillus subtilis.* In the cells of transformed *Bacillus subtilis,* a new hybrid plasmid pTTB32 is formed, which is then used to obtain a penicillinase producing transformant of *Bacillus stearothermophilus* in the same manner as described above.

As indicated above, gram-positive or gram-variable thermophilic bacteria, typically *Bacillus stearothermophilus,* can be transformed by receiving any of a variety of donor plasmids and grow at an elevated temperature while holding the replicable plasmid with sufficient stability in the cells, whereby genetic properties which the donor plasmid carrys can be expressed in the transformant cells. Thus, the host thermophilic bacteria which had been transformed in accordance with the process of the present invention inherit the character of the donor plasmid and produce the useful substance which the DNA gene of the plasmid codes for.

The useful substances are those excreted outside the cells or those accumulated inside the cell such as various enzymes, hormones, organic acids and antibiotics.

The host microorganisms can be transformed so as to produce a variety of hormons and interferons of eucaryocyte origin by inserting into the donor plasmid to be incorporated into the host cell a DNA, originated from an eucaryocyte of a higher creature, or a DNA, synthesized chemically or enzymatically on the basis of RNA transcribed from an eucaryocyte DNA.

The process of the present invention can also be utilized to convert a given substrate into a useful substance by incorporating the substrate into a culture medium in which the transformed bacteria grow. Thus, any type of biological reactions which has hitherto been utilized for converting various organic compounds, such as oxidation, reduction, cleavage, transition, isomerization, introduction and removal of various substituents and the like, can be achieved by the use of the transformant obtained in accordance with the process of the present invention. Organic substrates which may be converted microbiologically are various aliphatic, alicyclic, aromatic or heterocyclic compounds, for instance, terpenes, steroids, alkaloids, saccarides, amino acids, nucleic acids, peptides, naturally-occurring or semi-synthesized antibiotics, and other organic compounds.

In the following description, the process of the present invention will be elucidated in more detail by way of example.

EXAMPLE 1

(1) Preparation of plasmid:

A strain of *Bacillus subtilis,* which carries a plasmid pUB110 therein, was cultured in L broth (containing peptone 1%, yeast extract 0.5% and NaCl 0.5%, and being adjusted to pH 7.0) with shaking at 37° C. for 5 hours. The cells in their logarithmic growth phase were collected and bacteriolyzed by means of lysozyme/SDS treatment, and the treated cells were added with NaCl so as to make its final concentration being 1M and allowed to stand overnight at 4° C. The solution was centrifuged at 30,000×g for 30 minutes to give a supernatant. This supernatant was subjected to cesium chloride/ethidium bromide (CsCl-EdBr) equilibrium density gradient centrifugation to give a required fraction containing pUB110 plasmid DNA.

The obtained fraction was extracted with butanol so as to remove the remaining EdBr and dialized against tris-buffer (10 mM tris-HCl buffer, being adjusted to pH 7.5 and combined with 0.1 mM EDTA.Na) to give a plasmid DNA solution.

(2) Transformation of thermophilic bacteria by means of drug-resistant plasmid introduction:

A kanamycin-sensitive (hereinafter referred to as "Km$^s$") strain of *Bacillus stearothermophilus* ATCC 12980 CU12 was selected as a thermophilic bacterium.

The microorganisms were inoculated in LGS broth (20 ml, containing peptone 1%, yeast extract 0.5%, NaCl 0.5%, glucose 0.25% and sucrose 0.15M, and being adjusted to pH 7.2), and the inoculated medium was stirred at 55° C., while allowing the microorganisms to grow up to their logarithmic growth phase (OD$_{660}$≈0.4). The cells obtained by centrifugation were subsequently suspended in 1 ml of SMM-LG medium (containing sucrose 0.33M, maleic acid 0.02M, MgCl$_2$ 0.02M, peptone 1%, yeast extract 0.5%, NaCl 0.5% and glucose 0.25%, and being adjusted to pH 6.5). This suspension, after adding lysozyme thereto (1 μg/ml, final), was moderately stirred at 48° C. for 20 minutes and then centrifuged at 5000×g for 7 minutes to separate the formed protoplast. The latter was washed with 1 ml of SMM-LG medium, centrifuged at 5000×g for 7 minutes, and re-suspended in 1 ml of SMM-LG medium. The protoplast suspension thus obtained was used in the subsequent experiment.

The above-mentioned protoplast suspension (0.5 ml) was added to a mixed solution of 50 μl of the plasmid DNA solution prepared in accordance with the process described in (1) above, and 50 μl of a modified SMM solution whose concentration was twice as thick as SMM solution (containing sucrose 0.33M, maleic acid 0.02M and MgCl$_2$ 0.02M, and being adjusted to pH 6.5). Immediately thereafter, 1.5 ml of a PEG 6000 solution (40% polyethylene glycol in SMM solution) which had previously been kept at 48° C. was added to the mixture.

By gentle stirring, the protoplast in the mixture was allowed to aggregate, and the transfer of the plasmid into the protoplast was induced. Two minutes after the addition of PEG, 5 ml of SMM-LG medium was added, and the mixture was subjected to centrifugation at 5000×g for 7 minutes to separate the protoplast. The protoplast was suspended in 1 ml of SMM-LG medium containing 0.01% bovine serum albumin (BSA), and the suspension was stirred moderately at 48° C. for 90 minutes to accelerate the expression of the drug-resistant genes coded on the plasmid.

The protoplast suspension (100 μl) was mixed with 3 ml of an upper layer agar medium for regeneration (containing agar 0.6%, Bacto tryptone 1%, yeast extract 0.5%, NaCl 0.5%, casamino acid 0.01%, $KH_2PO_4$ 0.15%, $K_2HPO_4$ 0.45%, $MgCl_2$ 0.02M, glucose 0.5%, sucrose 0.2M and BSA 0.02%, and being adjusted to pH 7.3) containing 20 μg/ml of kanamycin and being kept at 50° C. The mixture was uniformly spread over a plate of 25 ml of a lower layer agar medium for regeneration (the same composition as the upper layer except that agar concentration was 2% instead of 0.5%) containing 20 μg/ml of kanamycin, and allowed to solidify thereon.

A number of colonies appearing on the agar plate after having been kept at 48° C. for 5-7 days were then isolated and cloned to give a pure culture.

The transformed strain thus obtained was resistant to kanamycin and was proved to have the plasmid pUB110 ($Km^r$) in its cell in contrast with the starting host microorganism.

Apart from this, a series of processes similar to those described above were performed on an agar medium for regeneration which did not contain kanamycin, and the number of the regenerated strains was counted. As a result of the counting, it was found that kanamycin resistant transformed strains was obtained in a frequency of about $1 \times 10^{-4}$ of the all regenerated strains.

(3) Stability of the transformed strain:

The results of the experiment on the stability of the kanamycin resistant genetic character of the transformed strains obtained in accordance with the process (2) above, are shown in Table 1 below.

The stability test was performed in the following manner. First, the transformed strains were pre-cultured at 48° C. on L broth containing 5 μg/ml kanamycin, diluted with L broth and inoculated into LG broth (L broth further containing 0.25% of glucose) in a manner that the initial organism number was about 50 cells/ml. The inoculated medium was incubated at 48° C., 55° C., 60° C. and 65° C., respectively, for about 20 generations. Thereafter, the cultured broth was used to form colonies on LG agar medium (L medium containing 1.5% agar) at 48° C., and each of the colonies was transplanted on LG agar medium containing 5 μg/ml kanamycin and its growth was observed.

TABLE 1

| Cultivation temperature (°C.) | Generation in growth | Percentage of colonies holding the character resistant to kanamycin (%) |
|---|---|---|
| (Preincubation, 48° C.) | — | 100 |
| 48 | 18 | 100 |
| 55 | 21 | 100 |
| 60 | 19 | 8 |
| 65 | 20 | 13 |

From the above results, it was confirmed that the stability of the transformed strain was sufficient at 48° C. and 55° C. but not sufficient at 60° C. and 65° C.

EXAMPLE 2

An experiment was carried out to prepare another plasmid DNA for use in the transformation of the thermophilic bacteria described in Example 1 (2), as follows:

(1) Preparation of a chromosomal DNA coding for a genetic character of penicillinase production:

*Bacillus licheniformis* ATCC 9945A FDO 120 C01, holding a constitutive genetic character of penicillinase production, were cultured in L broth (1 liter) at 37° C. for 5 hours. Cells at logarithmic growth phase were collected, washed with SCC solution (containing NaCl 0.15M and sodium citrate 0.015M, and being adjusted to pH 7) and suspended in 10 ml of TE buffer (containing trihydroxylaminomethane.HCL 0.02M, $EDTA.Na_2$ 1 mM, and being adjusted to pH 7.6) containing 20% sucrose.

After adding lysozyme (10 mg/ml, final) and holding at 37° C. for 10 minutes, this suspension was further combined with 20 ml of a lauroyl sarcosylate solution (1%) (prepared by dissolving the salt in a 0.1M EDTA.Na solution), subsequently with pronase (10 mg/ml) and kept at 50° C. until the solution turned clear. The solution was then subjected to CsCl-EdBr equilibrium density gradient ultracentrifugation to fractionate and collect the chromosomal DNA. Subsequently, butanol was added to the collected DNA fraction, and EdBr was removed therefrom by extraction. The fraction was dialyzed against TS buffer (0.02M trishydroxylamine and 0.15M NaCl, and being adjusted to pH 8.0) to give a chromosomal DNA solution.

(2) Preparation of vector DNA:

In order to clone a gene which controls penicillinase production, a plasmid pMB9 ($Tc^r$) which serves as a vector for the gene was extracted as follows:

First, a strain of *Escherichia coli* C600 which carries the plasmid pMB9 (commercially available from Bethesda Research Laboratories Inc.) was inoculated into one liter of glucose/casamino acid/inorganic salt broth (containing glucose 0.2%, $NH_4Cl$ 0.1%, $K_2HPO_4$ 0.3%, NaCl 0.5%, $MgSO_4.7H_2O$ 0.01%, $CaCl_2$ 0.0015% and casamino acid 2%, and being adjusted to pH 7.2). The inoculated medium was stirred at 37° C. for 3 hours, added with chloramphenicol (170 μg/ml, final) and continued to be cultured for subsequent 16 hours. This process multiplied the pMB 9 plasmid content in the microorganism cells. After completing the cultivation, cells in the broth were collected, bacteriolyzed by treating with lysozyme/SDS, and worked up in the same the manner as described in Example 1 (1), to obtain a DNA solution of the plasmid pMB9.

(3) Insertion of chromosomal DNA segment into the vector:

The chromosomal DNA solution (10 μg) obtained in accordance with the method described in (1) and the plasmid pMB9 solution (10 μg) described in (2) were respectively treated with endonuclease Eco Rl at 37° C. for 1 hour to cleave the circular DNA chain. After being subjected to heat treatment at 65° C. for 5 minutes, the solutions were combined and treated with T4 DNA ligase at 10° C. for 24 hours in the presence of ATP, dithiothreitol and $MgCl_2$. After having been subjected to second heat treatment at 65° C. for 5 minutes, there was added to the reaction solution a two fold volume of ethanol, and precipitated spliced DNA was collected.

(4) Transformation of *Escherichia coli* by means of a plasmid which carries a penicillinase producing gene:

*Echerichia coli* C600 strain sensitive to tetracycline (hereinafter referred to as "Tc$^s$") and to ampicillin (hereinafter referred to as "Ap$^s$") was inoculated in 10 ml of L broth. The inoculated medium was incubated with shaking at 37° C. up to a median logarithmic growth phase. The cells in the broth were collected and successively suspended under ice-cooling condition in a 0.1M MgCl$_2$ solution and then a 0.1M CaCl$_2$ solution, to obtain the so-called "competent cell" (capable of receiving an exogenous DNA). This cell suspension was combined with the DNA solution obtained in (3) above, and the mixture was allowed to react under ice-cooling condition for 30 minutes. Immediately thereafter, the mixture was subjected to heat treatment at 42° C. for 2 minutes, and then allowed to stand under ice-cooling for 30 minutes to accelerate the intake of DNA into the cells. The cell suspension was used to inoculate a fresh L broth, and the inoculated medium was incubated under shaking at 37° C. for 2 hours. Cells collected from this suspension were washed, spread over an L agar medium (containing agar 1.5%, tetracycline 20 µg/ml and ampicillin 20 µg/ml) and kept at 37° C. After two days, each of the clones was isolated therefrom by picking up the colonies formed on the medium. Each of the transformed strains thus obtained was different from the host microorganism and resistant to both tetracycline and ampicillin and capable of producing penicillinase.

A plasmid DNA was prepared by subjecting the transformed microorgasnism to the treatment described in (2), and the obtained plasmid DNA was treated with Eco Rl at 37° C. for 1 hour to cleave the DNA chain. An electrophoresis analysis of this DNA solution on a 1% agalose gel (prepared by using a solution containing trishydroxyaminomethane 0.089M, boric acid 0.989M and EDTA.Na$_2$ 2.5 mM) showed that a new DNA fragment of 2.8 Mdal was inserted into the vector plasmid pMB9 (3.5 Mdal). This shows that a gene controlling the penicillinase production is in the DNA fragment of 2.8 Mdal and is cloned with the vector plasmid pMB9 to give a new plasmid pTTE11. In other words, it shows that only the cells which have received the DNA fragment of 2.8 Mdal are selectively obtained.

(5) Preparation of plasmids pTB19 and pTB53 and transformation of thermophilic bacteria:

First, a sample obtained from the soil in the high temperature environment was inoculated in L broth (5 ml), and the inoculated medium was incubated at 55° C. for 4 hours under shaking. A portion (100 µl) of the cultured broth was then spread over 1.5% L agar medium (containing 25 µg/ml kanamycin or 25 µg/ml tetracycline) and kept at 55° C. for 20 hours. Cells in a pure state were separated from the resultant colonies by picking up and were cultured in L broth at 55° C. for about 5 hours under shaking. Cells collected from the broth in a logarithmic growth phase were bacteriolyzed by lysozyme/SDS treatment and added with NaCl (1M, final), and the mixture was allowed to stand overnight.

The solution was centrifuged at 30,000×g for 30 minutes to give a supernatant, which was then subjected to cesium chloride/ethidium bromide (CsCl-EdBr) equilibrium density centrifugation. A fraction containing the plasmid DNA was thus obtained.

An electrophoresis analysis of the plasmid DNA solution on a 1% agalose gel showed the formation of two species of plasmids. One having a smaller molecular weight was designated as pTB18 while the other (17.2 Mdal) as pTB19. Using a solution containing both of pTB18 and pTB19, the competent cells of Bacillus subtilis 168 were transformed in a conventional manner.

The screening of the transformed strain was performed at 37° C. on L broth containing agar (1.5%) and kanamycin (5 µg/ml) or tetracycline (25 µg/ml).

This screening gave a transformed strain resistant to both drugs. Identification by means of an agalose gel electrophoresis of a plasmid prepared from the transformed strain showed that the transformant held only pTB19. This fact indicates that only the pTB19 carries the genes resistant to both drugs.

The transformed strain could grow on an LGS medium containing kanamycin (5 µg/ml) or tetracycline (5 µg/ml) at temperature of 55° C., 60° C. or 65° C. This proves that the genes coding for drug-resistance have been successfully expressed in the transformant.

Next, *Bacillus subtilis* 168 was further transformed by introducing a plasmid obtained by cleaving the plasmid pTB19 (Km$^r$, Tc$^r$) with a restricting endnuclease Eco Rl and then combining the cleaved fragments using T4 DNA ligase.

Various plasmids were obtained from the transformant, and a plasmid (11.2 Mdal) which is resistant to both kanamycin and tetracycline and composed of the minimum DNA fragments was separated. The plasmid was designated as pTB53 (Km$^r$, Tc$^r$).

By cleaving pTB19 and pTB53 with various endnucleases and subjecting the resultant fragments to 0.7%, 1% and 1.4% agalose gel electrophoresis, the cleaving points maps shown in FIGS. 1 (A) and 1 (B) of the accompanying drawing were prepared.

*Bacillus stearothemophilus* ATCC 12980 CU12 strain was transformed in the same manner as in Example 1 (2) by the use of either pTB19 or pTB53 obtained above. The respective transformants thus obtained were found resistant to kanamycin contrary to the untreated receptor bacteria. This proves that these transformants carry pTB19 (Km$^r$) or pTB53 (Km$^r$).

(6) Transformation of *Bacillus subtilis* by means of plasmid which carries penicillinase producing gene:

Plasmid PTTE11 carrying the penicillinase producing gene was prepared from the transformed strain of *Escherichia coli* obtained by the method as described in (4). On the other hand, plasmid pTB53 (Km$^r$, Tc$^r$) was prepared by the method as described in (5).

Ten µg of plasmid pTB53 and 10 µg of pTTE11 were respectively treated with Eco Rl at 37° C. for 1 hour to cleave their DNA chains. After heat treatment at 65° C. for 5 minutes conducted for deactivating the Eco Rl, cleaved pTB53 and pTTE11 were combined and treated with T4 DNA ligase at 10° C. for 24 hours. After being subjected to heat treatment at 65° C. for 5 minutes, the reaction mixture was combined with two fold volume of ethanol. Precipitated DNA was collected and dissolved in a SSC solution. This DNA solution was used for transformation of a strain derived from *Bacillus subtilis*, Marburg 168 in the following manner.

The host microorganism was inoculated into 2 ml of Medium I (containing K$_2$HPO$_4$ 1.4%, KH$_2$PO$_4$ 0.6%, (NH$_4$)$_2$SO$_4$ 0.2%, sodium citrate 0.1%, MgSO$_4$.7H$_2$O 0.02%, glucose 0.5%, casamino acid 0.02% and tryptophane 50 µg/ml) with an inoculum size of 10$^8$ cell/ml, and the inoculated medium was incubated under shaking at 37° C. for 4 hours. The cultured broth (100 µl) is transferred to 1 ml of Medium II (contents of casamino acid, tryptophane and MgSO$_4$.7H$_2$O in Medium I were changed to 0.01%, 5 μg/ml and 5 μM, respectively), and the medium was incubated for 90 minutes to give competent cells. The suspension of this competent cells (0.9 ml) was combined with 0.1 ml of the donor DNA solution, and the mixture was stirred at 37° C. for 30 minutes and centrifuged. The collected cells were suspended again in L broth and incubated at 37° C. for 2 hours. After being diluted, the incubated broth was spread over L agar medium containing 5 μg/ml kanamycin and kept at 37° C. for 2 days.

Each of the colonies developed on the medium was isolated by means of picking up with a loop and the desired transformant was selected to the basis of penicillinase producing activity. A plasmid was extracted from the transformed strain in compliance with a known method and cleaved with Eco Rl in a manner similar to that described in (4) above. An electrophoresis analysis of the resultant fragments on agalose gel showed that a DNA fragment of the plasmid pTTE11 carrying penicillinase producing gene had been spliced into the vector plasmid pTB53 (11.2 Mdal). The complex plasmid was designated as pTTB32.

(7) Transformation of a thermophilic bacteria *Bacillus stearothermophilus* by means of the complex plasmid carrying the penicillinase producing gene:

In a manner identical to that described in Example 1 (2), a transformed strain (Km$^r$) was prepared by using *Bacillus stearothermophilus* ATCC 12980 CU12 as the host microorganism and the complex plasmid pTTB32, obtained in the method as described in (6) above, as the donor DNA. The transformed strain was found to exhibit a penicillinase producing activity.

(8) Productivity of penicillinase by various transformed strains:

The penicillinase producing activities were determined on *Bacillus licheniformis* ATCC 9945A FDO 120 which is a wild strain of penicillinase producing bacilli, CO1 strain which is a variant of the above strain and has a constitutive penicillinase producing activity, and various transformed strain obtained by the transformation with a plasmid carrying a penicillinase producing gene. Thus, each of the above microorganisms was inoculated into L broth. The inoculated medium was cultured at a temperature shown in Table 2, and the penicillinase producing activity at a logarithmic growth phase was determined in terms of penicillinase unit. The results are shown in Table 2.

TABLE 2

| Microorganism | Cultivation temperature (°C.) | Penicillinase units/ dry weight of microorganism (mg) |
|---|---|---|
| 1. *Bacillus licheniformis* ATCC 9945A, FDO 120 | 37 | 7.1 |
| 2. *Bacillus licheniformis* ATCC 9945A, CO1 | 37 | 2970 |
| 3. *Escherichia coli* C600 | 37 | 0 |
| 4. *Escherichia coli* (pMB9) | 37 | 0 |
| 5. *Escherichia coli* (pTTE11) | 37 | 6.7 |
| 6. *Bacillus subtilis* 168 | 37 | 1.0 |
| 7. *Bacillus subtilis* (pTTB32) | 37 | 12000 |

TABLE 2-continued

| Microorganism | Cultivation temperature (°C.) | Penicillinase units/ dry weight of microorganism (mg) |
|---|---|---|
| 8. *Bacillus stearothermophilus* ATCC 12980 CU12 | 50 | 0 |
| 9. *Bacillus stearothermophilus* ATCC 12980 CU12 (pTTB32) | 50 | 9000 |

EXAMPLE 3

According to the method described in Example 2, *Bacillus stearothermophilus* was transformed using each of *Bacillus cereus* ATCC 21768-21772, *Bacillus licheniformis* ATCC 27811 and *Bacillus subtilis* 6051a as a donor bacterium. An enzyme-producing ability of each of the resulting transformants was determined by the starch-iodine reaction, and all of the transformants proved to have an α-amylase producing ability.

EXAMPLE 4

(1) Transformation of a thermophilic bacterium *Bacillus stearothermophilus* carrying a cryptic plasmid pBS02 with a plasmid pUB110 resistant to kanamycin:

A plasmid having a molecular weight of about 19.8×10$^6$ was obtained from a S2 strain derived from *Bacillus stearothermophilus* ATCC 12980 CU12 by CsCl-EdBr equilibrium density gradient centrifugation. It was found that the obtained plasmid is cryptic and had no selected marker such as drug resistance. Therefore, *Bacillus stearothermophilus* S2 strain carrying a cryptic plasmid pBS02 was transformed with a plasmid pUB110 (Km$^r$) which had originated from *Staphylococcus aureus* and had been extracted from *Bacillus subtilis* according to the method described in Example 1 (2).

(2) Extraction of recombinant plasmid from the transformed strain:

A plasmid was extracted from the transformed strain obtained in (1) above according to the method described in Example 1 (1). An electrophoresis analysis of the obtained plasmid on an agalose gel showed that it was neither pUB110 (Km$^r$) (3.0 Mdal) nor pBS02 (19.8 Mdal) and had a larger molecular weight than those of the plasmids given above. This new combinant plasmid was designated as pBSK1 (21.5 Mdal).

The transformation of *Bacillus stearothermophilus* with the plasmid pBSK1 using the method described in (1) above gave a transformant resistant to kanamycin. This showed that pBSK1 carries a gene coding for kanamycin resistant property.

By cleaving pBS02 and pBSK1 with an endonuclease Bam HI and treating the obtained fragments in the same manner as in Example 1 (5), the cleaving site maps shown in FIGS. 2 (A) and 2 (B) of the accompanying drawing were prepared. These maps show that a gene fragment (1.7 Mdal) coding for kanamycin resistance and derived from pUB 110 has been inserted into a gene fragment (5.6 Mdal) derived from pBS02 as a result of the transformation.

(3) Stability of pUB110 and pBSK1 in thermophilic bacterium cell:

Stability test on *Bacillus stearothermophilus* S2 strain carrying pUB110 or pBSK1 was conducted in the same manner as described in Example 1 (3). The results are shown in Table 3.

TABLE 3

| Strain | S2 strain carrying pUB110 | | S2 strain carrying pBSK1 | |
|---|---|---|---|---|
| Cultivation temperature (°C.) | Generation in growth | Km$^r$ colonies (%) | Generation in growth | Km$^r$ colonies (%) |
| (Pre-incubation, 48° C.) | — | 100 | — | 100 |
| 48 | 18 | 100 | 17 | 97 |
| 55 | 21 | 100 | 18 | 97 |
| 60 | 19 | 8 | 19 | 97 |
| 65 | 20 | 13 | 18 | 99 |

The table shows that the transformant with a plasmid pUB110 is unstable at a temperature above 60° C., while the transformant with a plasmid pBSK1 is stable between 48°–65° C. Thus, it was confirmed that the recombinant plasmid pBSK1 is stable at 65° C. and contains a gene coding for kanamycin resistance.

What is claimed is:

1. A process for the transformation of a microorganism of the species *Bacillus stearothermophilus*, which microorganism is thermophilic and is gram-positive or gram-variable, which comprises introducing into said microorganism, which is in the protoplast state at a temperature of about 40° to 70° C., a plasmid comprising the vector pTB 19, said plasmid having been retained in *Bacillus subtilis* FERM-P5895.

* * * * *